United States Patent
Choi et al.

(10) Patent No.: US 10,675,237 B2
(45) Date of Patent: *Jun. 9, 2020

(54) COSMETIC CONTAINING FOAM AS CARRIER

(71) Applicant: AMOREPACIFIC CORPORATION, Seoul (KR)

(72) Inventors: Jung Sun Choi, Yongin-si (KR); Kyung Ho Choi, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/109,384

(22) Filed: Aug. 22, 2018

(65) Prior Publication Data

US 2018/0360730 A1 Dec. 20, 2018

Related U.S. Application Data

(63) Continuation of application No. 15/302,047, filed as application No. PCT/KR2015/003646 on Apr. 10, 2015, now Pat. No. 10,092,498.

(30) Foreign Application Priority Data

Apr. 10, 2014 (KR) ........................ 10-2014-0043005

(51) Int. Cl.
| | |
|---|---|
| *A61K 8/81* | (2006.01) |
| *A45D 37/00* | (2006.01) |
| *A61Q 1/04* | (2006.01) |
| *A61Q 1/10* | (2006.01) |
| *A61Q 17/04* | (2006.01) |
| *A61Q 19/00* | (2006.01) |
| *A61K 8/02* | (2006.01) |
| *A61K 8/06* | (2006.01) |
| *A61K 8/04* | (2006.01) |

(52) U.S. Cl.
CPC ............ *A61K 8/8194* (2013.01); *A45D 37/00* (2013.01); *A61K 8/0204* (2013.01); *A61K 8/0279* (2013.01); *A61K 8/046* (2013.01); *A61K 8/06* (2013.01); *A61Q 1/04* (2013.01); *A61Q 1/10* (2013.01); *A61Q 17/04* (2013.01); *A61Q 19/00* (2013.01); *A61K 2800/546* (2013.01); *A61K 2800/87* (2013.01)

(58) Field of Classification Search
CPC .. A61K 8/0208; A61K 2800/87; A61K 8/046; A61K 8/8194; A61K 8/87; A61K 2800/10; A61K 8/0204; A61K 8/8123; A61K 8/85; A61K 8/86; A61Q 19/00; A61Q 17/04; A61Q 1/02

See application file for complete search history.

(56) References Cited

U.S. PATENT DOCUMENTS

| | | |
|---|---|---|
| 2014/0023689 A1 | 1/2014 | Kim et al. |
| 2014/0341959 A1 | 11/2014 | Choi et al. |
| 2015/0078802 A1 | 3/2015 | Choi et al. |
| 2015/0117931 A1 | 4/2015 | Jung et al. |
| 2015/0118269 A1 | 4/2015 | Choi et al. |

FOREIGN PATENT DOCUMENTS

| | | | | |
|---|---|---|---|---|
| EP | 2837305 | * | 4/2013 | ............. A45D 34/00 |
| EP | 2837305 | | 2/2015 | |
| EP | 2837374 A1 | | 2/2015 | |
| JP | 1988196612 | | 12/1988 | |
| JP | 1988199706 | | 12/1988 | |
| JP | 02080257 U | | 6/1990 | |
| JP | 08164019 A | | 6/1996 | |
| JP | 08266329 | | 10/1996 | |
| JP | 200079016 A | | 3/2000 | |
| JP | 3187673 B2 | | 5/2001 | |
| JP | 2003192826 | | 7/2003 | |
| JP | 2003199425 | | 7/2003 | |
| KR | 1020130083852 A | | 7/2013 | |
| KR | 10-2013-0116043 | * | 10/2013 | ............. A45D 34/00 |
| KR | 1020130116043 A | | 10/2013 | |
| KR | 1020130116182 A | | 10/2013 | |
| KR | 1020130116205 A | | 10/2013 | |

OTHER PUBLICATIONS

Decision of Final Rejection—Japanese Patent Application No. 2016-561816 dated Nov. 12, 2018, citing reference listed witin.
International Search Report with English Translation for International Application No. PCT/KR2015/003646 dated Jul. 21, 2015.
Japanese Office Action—Japanese Application No. 2016-561816 dated Jun. 12, 2018, citing references listed within.
Supplementary European Search Report for Application No. 15776533.0 dated Dec. 19, 2017.
Written Opinion for International Application No. PCT/KR2015/003646 dated Jul. 21, 2015.

* cited by examiner

*Primary Examiner* — Audrea B Coniglio
(74) *Attorney, Agent, or Firm* — Rothwell, Figg, Ernst & Manbeck, P.C.

(57) ABSTRACT

The present invention relates to a cosmetic comprising an acrylonitrile-butadiene rubber (NBR) as a carrier of a cosmetic composition and, specifically, to a cosmetic comprising a foam carrier and a cosmetic composition loaded on the foam carrier, wherein the foam carrier contains an NBR, includes pores with an average size of 200-900 μm, and has a thickness of 1-50 mm, and wherein the cosmetic composition has a viscosity of 2,000-60,000 cps. The present invention has excellent filling ability, loading ability, and discharging ability with respect to the liquid-phase cosmetic composition, and thus facilitates carrying a liquid-phase cosmetic composition with low viscosity to high viscosity.

16 Claims, 2 Drawing Sheets

[Fig. 1]
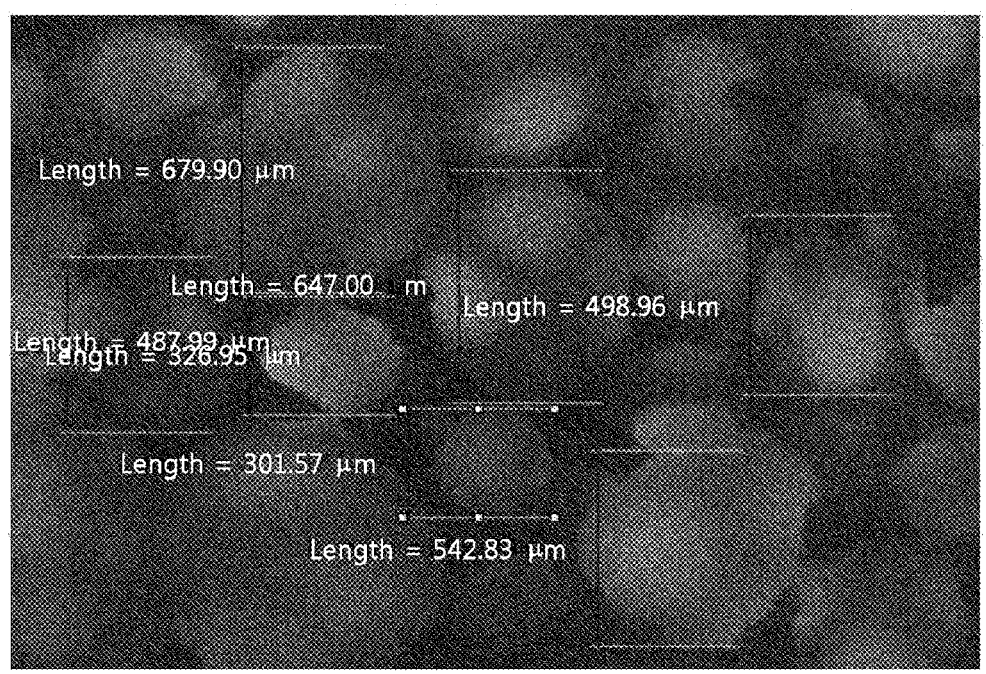
[Fig. 2]
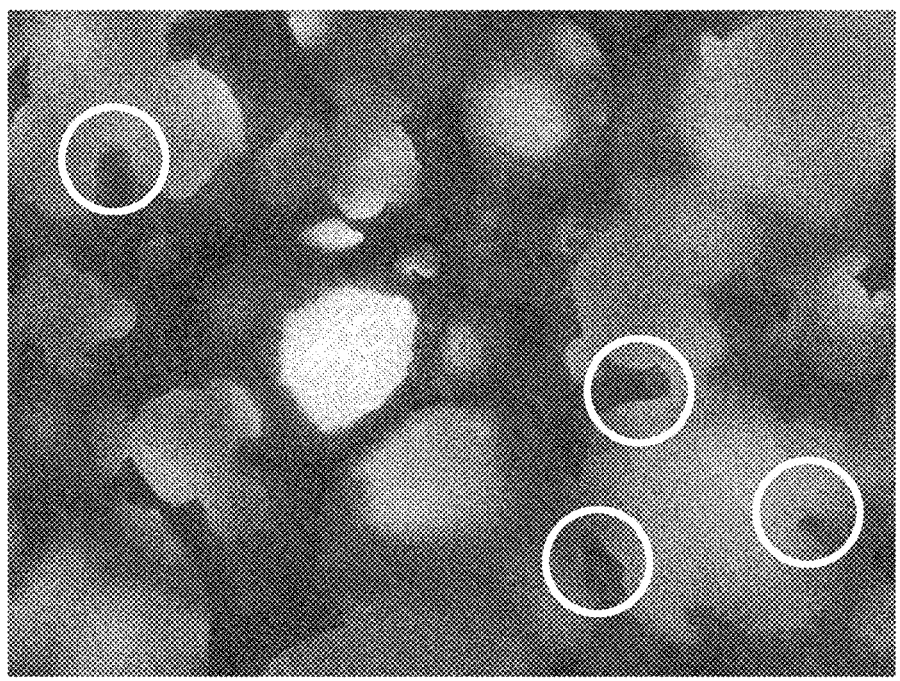

[Fig. 3]
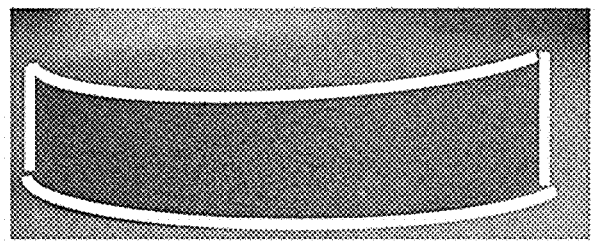
[Fig. 4]
| Material | NBR | NBR |
|---|---|---|
| Average pore size (μm) | 150 | 600 |
| Pore image Nikon ECLIPSE LV100POL 5X0.15 | | |
| Reference | Small pore size | Large pore size and bumps |
| Hardness (Asker F hardness) | 50 | 50 |
| Packability | X | ○ |
| Supportability | ○ | ○ |
| Releasability | X | ○ |
◎ : excellent, ○ :good, △ : satisfactory, X : poor

COSMETIC CONTAINING FOAM AS CARRIER

CROSS REFERENCE TO RELATED APPLICATIONS

This application is a continuation of U.S. application Ser. No. 15/302,047, filed on Oct. 5, 2016, which is a National Stage application of PCT/KR2015/003646, filed Apr. 10, 2015, which claims the benefit of Korean Patent Application No. 10-2014-0043005, filed on Apr. 10, 2014, each of which is incorporated by reference in their entirety herein.

TECHNICAL FIELD

The present disclosure relates to a cosmetic product including acrylonitrile-butadiene rubber (also referred to as "NBR" hereinafter) as a carrier for a cosmetic composition.

BACKGROUND ART

In general, liquid cosmetic compositions have been distributed and stored while being packed in vacuum containers, pump containers or glass containers according to the related art. However, such containers have a disadvantage in that they have low portability. Recently, there has been an increasing need for easily carrying out and modifying beauty make-up during outdoor activity, and thus a carrier for an easily portable liquid cosmetic composition has been increasingly in demand.

Typical containers in which a liquid cosmetic composition can be carried with ease include a pact-type container. To allow a liquid cosmetic composition to be received in a pact-type container, the following may be considered: whether the carrier for a cosmetic composition is for use in such a container or not, whether a cosmetic composition can be packed well in the carrier or not, whether the carrier can support the cosmetic composition uniformly for a long time or not, and whether the cosmetic composition can be released in an adequate amount when it is taken from the carrier to an applicator or not. In addition, it is preferred that the carrier includes a material strongly resistant against bacterial contamination because it is exposed continuously to the exterior and is in contact with an applicator during use.

According to the related art, NBR having a small pore size provides a vacant space that is not sufficient to support a composition therein, and thus a cosmetic composition cannot be packed in NBR sufficiently. Moreover, even when a cosmetic composition is packed in NBR, NBR having a high swelling ratio causes deformation of sponge and does not allow smooth release of a cosmetic composition. Further, NBR is problematic in that it cannot maintain its antibacterial effect against external bacteria. As a result, NBR has not been used as a carrier but as an applicator, such as, puff. Polyurethane allows fine release of a cosmetic composition so that users may carry out thin and uniform beauty make-up. However, since it shows a low skin covering effect, consumer's likes and dislikes are clear.

Meanwhile, in the case of NBR in the form of foam, it has been reported that NBR foam may be used as an applicator for pump containers, glass containers or vacuum containers. However, NBR foam used as an applicator according to the related art has no sufficient supportability and releasability as a carrier for a pact type product (Japanese Patent Publication No. 3,187,673, Japanese Laid-Open Patent No. 2000-0079016, and Korean Laid-Open Patent No. 2013-0116043).

REFERENCES

Patent Documents

Japanese Patent Publication No. 3,187,673
Japanese Laid-Open Patent No. 2000-0079016
Korean Laid-Open Patent No. 2013-0116043

DISCLOSURE

Technical Problem

A technical problem to be solved by the present disclosure is to provide a carrier which has excellent packability, supportability and releasability to cosmetic compositions having different viscosities so that liquid cosmetic compositions may have high portability and cosmetic compositions having a high skin covering effect may be packed therein.

Technical Solution

In one general aspect, there is provided a cosmetic product, including:
a foam carrier; and
a cosmetic composition supported in the foam carrier,
wherein the foam carrier includes acrylonitrile-butadiene rubber (NBR), is provided with pores having an average size of 200-900 μm and has a thickness of 1-50 mm, and the cosmetic composition has a viscosity of 2,000-60,000 cps.

Advantageous Effects

The foam carrier included in the cosmetic product according to the present disclosure has excellent properties required for a carrier for a liquid cosmetic composition, including packability, supportability and releasability. Particularly, since the NBR foam forming the carrier has an optimized pore size and thickness in addition to the bump structure and cell-in-cell structure thereof, it can stably pack and support liquid cosmetic compositions having a different range of viscosities and can release an adequate amount of liquid cosmetic composition having a different viscosity range even with a light touch to the foam during use. Therefore, the cosmetic product according to the present disclosure provides a liquid cosmetic composition with easy portability, and thus realizes excellent color developing, covering, moisturizing, application feel and elasticizing effects on the skin.

DESCRIPTION OF DRAWINGS

FIG. 1 and FIG. 2 are photographs of NBR foam according to an embodiment of the present disclosure as taken by an optical microscope.

FIG. 3 shows the lateral surface of NBR foam according to an embodiment of the present disclosure, as processed into the form of a coating film.

FIG. 4 shows the results for a releasability test on each of the NBR foam having an average pore size of 150 μm and the NBR foam having an average pore size of 600 μm.

BEST MODE

As used herein, "carrier" means a material by which any material or ingredient, such as a composition, can be supported, and is used interchangeably with "support", "impregnation material" or "medium". In addition, "carrier"

may be used to release the material supported therein to a separate applicator. For example, the composition supported in the carrier may be transferred to the skin through a hand or an application means (also referred to as an applicator or application tool), such as puff, tip or brush.

As used herein, "supportability" means ability of holding and retaining any material or ingredient. The supportability required for a carrier is different from taking a material transiently on an applicator in that the supportability relates to supporting a composition uniformly for a long time.

As used herein, "packability" or "packing effect" means ability of packing a cosmetic composition in foam and may be expressed by the time required for packing a predetermined amount of cosmetic composition in foam. Herein, measurement of "packability" or "packing effect" relates to the time required for packing a cosmetic composition having a viscosity of 2,000-60,000 cps manually in NBR foam having a size of circle diameter 44 mm×height 9.0 mm.

As used herein, "releasability" or "releasing effect" means the amount of cosmetic composition released when taking the cosmetic composition by an applicator from the foam in which the cosmetic composition is supported. It is preferred for the foam to release the cosmetic composition in an adequate amount neither too little nor too much. Herein, measurement of "releasability" or "releasing effect" relates to the value obtained when compressing the surface of NBR foam including a cosmetic composition having a viscosity of 2,000-60,000 cps supported therein and having a size of circle diameter 44 mm×height 9.0 mm under a weight (force) of 2 kg.

As used herein, "durability" means how long the foam having a cosmetic composition supported therein maintains its shape without melting, tearing or swelling when the foam is allowed to stand at a predetermined temperature for a predetermined time, and/or how much the foam resist against repeated pressure applied by an applicator when the cosmetic composition is taken by the applicator from the foam.

The foam disclosed herein has excellent packability to a cosmetic composition, shows excellent supportability to a cosmetic composition with high uniformity for a long time, provides high releasability of an adequate amount of cosmetic composition when a cosmetic composition is taken, and maintains excellent durability even after supporting a cosmetic composition.

As used herein, "Asker F hardness" means hardness as determined by ASKER DUROMETER Type F (a hardness measuring system available from ASKER), and relates to hardness before a composition is supported in foam.

Hereinafter, the present disclosure will be explained in more detail.

In one aspect, there is provided a cosmetic product, including:
a foam carrier; and
a cosmetic composition supported therein,
wherein the foam carrier includes acrylonitrile-butadiene rubber (NBR), is provided with pores having an average size of 200-900 μm and has a thickness of 1-50 mm, and the cosmetic composition has a viscosity of 2,000-60,000 cps.

According to some embodiments, the foam carrier may include acrylonitrile-butadiene rubber (NBR) in an amount of at least 80 wt %, at least 85 wt %, at least 90 wt %, at least 93 wt %, at least 95 wt %, at least 97 wt %, at least 98 wt %, at least 99 wt % or 100 wt % based on the total weight of foam, but is not limited thereto. Hereinafter, the foam carrier including NBR is also referred to as "NBR foam" or "NBR foam carrier".

Herein, the pores included in the NBR foam carrier may have an average size of 200-900 μm. Particularly, the average pore size may be 900 μm or less, 800 μm or less, 700 μm or less, 600 μm or less, 500 μm or less, 400 μm or less, 300 μm or less, or 200 μm or less, and 200 μm or more, 300 μm or more, 400 μm or more, 500 μm or more, 600 μm or more, 700 μm or more, 800 μm or more, or 900 μm or more.

Herein, the average pore size of NBR foam may be determined by using an optical microscope (Nikon ECLIPSE LV100POL) at a magnification of 5×/0.15, as shown in FIG. 1.

When the average pore size of NBR foam is less than 200 μm, the NBR foam has an insufficient pore space in which a cosmetic composition is supported, resulting in low supportability. When the average pore size of NBR foam is larger than 900 μm, the pore space is excessively large, resulting in degradation of cosmetic composition releasability. Thus, the NBR foam according to the present disclosure having a large average pore size controlled to the above-defined range provides high air permeability, cushioning effect, softness, flexibility and elasticity.

According to an embodiment, the NBR foam having an average pore size of 200-900 μm particularly has an Asker F hardness of 10-95 before supporting a cosmetic composition. When the foam has a hardness less than 10, it is too soft to support its contents with a uniform distribution, and releases a cosmetic composition excessively. When the foam has a hardness larger than 95, it is too hard to pack a cosmetic composition, and hardly releases a cosmetic composition. In this context, the NBR foam according to the present disclosure may have an Asker F hardness of 95 or less, 90 or less, 80 or less, 70 or less, 60 or less, 50 or less, 40 or less, 30 or less, 20 or less, or 10, and 10 or more, 20 or more, 30 or more, 40 or more, 50 or more, 60 or more, 70 or more, 80 or more, 90 or more, or 95. The NBR foam having an average pore size of 200-900 μm has excellent packability, releasability and supportability to a cosmetic composition. Preferably, when the NBR foam has an Asker F hardness of 10-95, it shows increased supportability, packability and releasability to a cosmetic composition having a viscosity of 2,000-60,000 cps (centipoise). Although the NBR foam used herein has a relatively large average pore size of 200-900 μm, it includes bumps at the pore stems as shown in FIG. 2, and thus causes no precipitation of a composition even when it supports a low-viscosity composition.

According to an embodiment, the pores having bumps may be present in 20-80% based on the total number of pores included in the foam carrier. Particularly, the proportion of the pores having bumps may be 20% or more, 30% or more, 40% or more, 50% or more, 60% or more, 70% or more, or 80%, and 80% or less, 70% or less, 60% or less, 50% or less, 40% or less, 30% or to less, or 20%. When the bumps are present in an amount less than 20% of the total pores, precipitation may occur and the foam may have low durability. When the bumps are present in an amount of larger than 80% of the total pores, formation of pores is insufficient so that an excessively large amount of a cosmetic composition may be released. In addition, the bump may have a size corresponding to 2.5-25% of the average pore size. The bump size may be evaluated by measuring the length of a longer side of bump as taken by an optical microscope (Nikon ECLIPSE LV100POL) at a magnification of 5×/0.15.

Moreover, the NBR foam according to the present disclosure may have a cell-in-cell structure, which means a structure having a small-size cell contained in a large-size cell. Such a structure is a small-size cell formed at the framework or backbone (or stem) of a cell in addition to macropores formed during the foaming. The foam carrier having a cell-in-cell structure according to the present disclosure allows a cosmetic composition to be taken with a small thickness over a large area of an applicator (e.g. puff) without agglomeration when the cosmetic composition is taken by the applicator, and thus can transfer the cosmetic composition uniformly to the skin without agglomeration. Further, even when a low-viscosity cosmetic composition is supported, such a cell-in-cell foam structure prevents the precipitation of composition and realizes an excellent and high-concentration beauty make-up effect, including excellent color developing, skin covering, moisturizing, application feel and elasticizing effects.

Herein, viscosity may be determined by using a viscometer, such as Brookfield ULTRA, by using a spindle No. 63 at a spindle speed of 5 rpm, in the case of a liquid cosmetic composition.

According to an embodiment, the NBR foam carrier may have a thickness of 1-50 mm. When the foam has a thickness less than 1 mm, it cannot support a sufficient amount of cosmetic composition. When the foam has a thickness larger than 50 mm, it is difficult to release a cosmetic composition without residue of contents during use. For example, the carrier using the NBR foam according to an embodiment of the present disclosure may have a thickness of 3-45 mm, such as 5-40 mm, particularly 8-35 mm, and more particularly 10-30 mm. Specifically, the carrier may have a thickness of 50 mm or less, 40 mm or less, 30 mm or less, 20 mm or less, 10 mm or less, or 5 mm or less, and 1 mm or more, 10 mm or more, 20 mm or more, 30 mm or more, 40 mm or more, or 50 mm or more.

According to an embodiment, the NBR foam has a controlled density so that it may have a space in which a cosmetic composition is supported. When the NBR foam has a density of 0.05-1.25 $g/cm^3$, it is possible to ensure a space sufficient to support a cosmetic composition within the NBR foam and to provide excellent durability. When the NBR foam has a density less than 0.05 $g/cm^3$, the foam has a low solid content and poor tensile strength, elasticity, hardness and durability so that it may be torn. In this case, it is not possible to form such large pores having a size of 200-900 µm. In addition, it is not possible to retain a cosmetic composition inside the pores due to its weak framework serving as a support, thereby causing degradation of supportability and thus precipitation. When the NBR foam has a density larger than 1.25 $g/cm^3$, it has a high solid content and the proportion of solid content based on the total volume is high, thereby providing a small space occupied by air, i.e., low porosity. Therefore, in this case, the foam has a decreased volume in which the contents are supported.

The NBR according to some embodiments of the present disclosure may have anti-bacterial property.

In addition, the NBR is a material based on an unsaturated nitrile monomer, such as acrylonitrile or methacrylonitrile, and a conjugated diene monomer, such as butadiene or isoprene. The NBR is obtained by copolymerization of a monomer composition via a polymerization process, such as emulsion polymerization, wherein the monomer composition is obtained by blending the base materials optionally with a predetermined amount of copolymerizable unsaturated monomers and adding an emulsifier, such as an anionic surfactant, or a polymerization initiator and a small amount of other additives, such as a molecular weight modifier.

According to an embodiment, the blending ratio of the unsaturated nitrile monomer to the conjugated diene monomer in the NBR is such a ratio that the amount of unsaturated nitrile monomer may be about 15-50 wt %. The blending ratio may be controlled depending on the use and cosmetic composition to be impregnated. According to another embodiment, the NBR may be carboxylated NBR obtained by further copolymerizing a third ingredient, such as acrylic acid, methacrylic acid, maleic acid, fumaric acid or itaconic acid and introducing carboxyl groups into the molecule.

As the NBR foam carrier according to an embodiment of the present disclosure supports a cosmetic composition, the vacant space within the carrier is occupied by the cosmetic composition while the carrier undergoes swelling. The degree of swelling may be varied with the material, hardness and additives, and the swelling ratio may be calculated according to the following Mathematical Formulae 1 and 2:

Height swelling ratio (%)=(Height of carrier after supporting contents−Initial height of carrier)/ Initial height of carrier*100     [Mathematical Formula 1]

Diameter swelling ratio (%)=(Diameter of carrier after supporting contents−Initial diameter of carrier)/Initial diameter of carrier*100     [Mathematical Formula 2]

According to an embodiment, the NBR foam carrier according to the present disclosure may satisfy at least one of the following swelling ratio conditions: a height swelling ratio of 2%-25% after supporting a cosmetic composition, and a diameter swelling ratio of 2%-25% after supporting a cosmetic composition. When the height swelling ratio is larger than 25% or the diameter swelling ratio is larger than 25%, the carrier may be swelled so that the upper cover of a container may be contaminated with the contents or the foam may not fit well with its container. When the height swelling ratio is lower than 2%, the foam has poor flexibility, resulting in low packability. In other words, when the swelling ratio is 2-25%, the foam is swelled with the contents and is wet sufficiently with the contents.

According to an embodiment, the NBR foam carrier may have a packability of 3-10 seconds, wherein the packability is defined as the time required for packing 15 g of a cosmetic composition manually in the foam carrier. In addition, supportability is defined as the amount of cosmetic composition carried by the foam carrier after packing the cosmetic composition therein. The NBR foam carrier may have a supportability of 85-99% based on the total weight of cosmetic composition packed in the foam carrier. Further, releasability is defined as the amount of cosmetic composition paid off when the cosmetic composition is taken (paid-off) by an application unit from the foam carrier. The NBR foam carrier may have a releasability of 0.2-0.7 g. The releasability is a value determined by compressing the surface of NBR foam impregnated with a cosmetic composition having a viscosity of 2,000-60,000 cps and having a size of circle diameter 44 mm×height 9.0 mm under a weight (force) of 2 kg. When the releasability is less than 0.2 g, the amount of cosmetic composition taken by an applicator is too small to provide convenience during use. When the releasability is larger than 0.7 g, the amount of cosmetic composition taken by an applicator is too large to form a uniform beauty make-up film on the skin.

According to an embodiment, the cosmetic composition may be liquid having a different range of viscosities and may include solution, emulsion, gel, cream or suspension. A liquid cosmetic composition is more difficult to carry and store as compared to a solid cosmetic composition. However, when using the carrier for a cosmetic composition according to the present disclosure, it is possible to store and carry a liquid cosmetic composition and creamy cosmetic composition stably and safely.

According to an embodiment, the cosmetic composition in the form of liquid or cream may be supported in the carrier so that any change in physical properties of the composition caused by thermal or physical impact may be reduced. In addition, since the carrier serves as a trap for its contents during use, it is possible to pay off an adequate amount of contents.

The cosmetic composition may include solution, emulsion or suspension, but is not limited thereto. In addition, the cosmetic composition supported in the NBR foam according to an aspect of the present disclosure may include a skincare cosmetic agent, make-up cosmetic agent containing a pigment, haircare cosmetic agent and a UV protecting agent, but is not limited thereto.

Particularly, the cosmetic composition applicable to the carrier for a cosmetic composition according to the present disclosure may be a water-in-oil (W/O) type or oil-in-water (O/W) type composition, or a dispersion type, particularly oil dispersion or water dispersion type composition In addition, the carrier for a cosmetic composition according to the present disclosure may have a coating film (closed cells) on at least one surface of the bottom surface (surface opposite to the surface that is in contact with the hand or applicator) and lateral surfaces, as shown in FIG. 3. The coating film prevents a cosmetic composition from escaping downwardly or laterally while the cosmetic composition is supported in the carrier. When the carrier has a lateral surface or bottom surface in the form of a coating film as described above, it is possible to inhibit the cosmetic composition from moving toward the lateral surface or bottom surface and flowing out to the exterior of the carrier. In this manner, it is possible to reduce the loss of a cosmetic composition, resulting in elongation of service life and improvement of convenience.

According to an embodiment, particular examples of the cosmetic composition may be formulated into a twin cake, make-up primer, make-up base, liquid or high-viscosity foundation, concealer, lipstick, lip gloss, powder, lip liner, eyebrow, eye liner, eye shadow, blusher, UV protecting agent, lotion, cream or essence, or the like, but is not limited thereto.

In addition, the cosmetic product according to some embodiments of the present disclosure may further include an applicator by which a cosmetic composition is taken from the foam carrier impregnated with the cosmetic composition. The cosmetic product may further include a cosmetic container so-called 'pact', which is a container including a lower part in which the carrier for a cosmetic composition is received and an upper part optionally having a mirror and serving as a lid, but is not limited thereto.

The examples will now be described to illustrate the present disclosure in detail. It will be appreciated by those skilled in the art that the following examples are for illustrative purposes only and not intended to limit the scope of the present disclosure.

EXAMPLES

First, NBR as a main ingredient, a pigment, a vulcanizing agent, and optionally a foaming agent and other additives are compounded with water at a predetermined ratio and blended under agitation to carry out foaming. Next, the foamed product is introduced to and cured in a mold, heated in a heating furnace to carry out vulcanization simultaneously with molding. Then, the resultant product is cut, dried and surface-treated to provide NBR foam.

The thus obtained NBR foam has an Asker hardness of 48 and an average pore size of 680 μm.

Test Example 1

1-1: Determination of Supportability, Releasability and Packability of NBR Foam Depending on Density In this test, the supportability, packability and releasability of NBR foam are determined as a function of density.

The cosmetic composition of Table 1 having a viscosity of 15,000 cps (as measured by Brookfield DV-III ULTRA, spindle No. 63, spindle speed 5 rpm) is supported in NBR foam that has an Asker F hardness of 5-95 before supporting the cosmetic composition. Then, the supportability, releasability and packability are determined.

The packability is determined by measuring the time required for packing 15 g of cosmetic composition manually in NBR foam (the packing is carried out by introducing the carrier to a container and packing the cosmetic composition in the carrier with a spatula). The supportability is determined by measuring the amount of cosmetic composition carried by the carrier in a container after packing 15 g of the cosmetic composition in NBR foam and allowing the NBR foam to stand at 55° C. for 4 weeks. The releasability is determined by measuring the amount of contents when taking the contents by a hand or puff from each type of foam.

The results are shown in Table 2.

TABLE 1

Constitution of Cosmetic Composition Supported in Foam

| | Item | Ingredients | Amount (wt %) |
|---|---|---|---|
| Oil phase ingredients | Oily ingredients | Ozokerite | 2.0 |
| | Oily ingredients | Dicaprylyl carbonate | 10.00 |
| | Preservative | Methyl paraben | 0.100 |
| | UV protecting agent | Octylmethoxy cinnamate | 7.000 |
| | UV protecting agent | Isoamyl-P-methoxycinnamate | 2.000 |
| | Pigment | Disteadimonium hectorite | 1.50 |
| | Oily ingredient | Decametylcyclopentasiloxane | 16.00 |
| | Emulsifier | Sorbitan sesquioleate | 2.000 |

TABLE 1-continued

Constitution of Cosmetic Composition Supported in Foam

| | Item | Ingredients | Amount (wt %) |
|---|---|---|---|
| | Emulsifier | LaurylPEG.PPG-18.18 methicone | 1.500 |
| | Pigment | Polymethyl methacrylate | 5.00 |
| | Pigment | Titanium dioxide/aluminum hydroxide/stearic acid | 7.00 |
| Aqueous phase ingredients | | Water | To 100 |
| | Moisturizing agent | Glycerin | 8.000 |
| | Emulsion stabilizer | Salt | 1.00 |
| | | Fragrance | 0.400 |
| | | Total | 100.000 |

TABLE 2

Supportability, Releasability and Packability of NBR Foam Depending on Density

| | Foam density before supporting | | | | | | | | | | | | | | |
|---|---|---|---|---|---|---|---|---|---|---|---|---|---|---|---|
| | 0.01 | 0.05 | 0.1 | 0.2 | 0.3 | 0.4 | 0.5 | 0.6 | 0.7 | 0.8 | 0.9 | 1.0 | 1.1 | 1.2 | 1.3 |
| Supportability (g) | 12.0 | 13.5 | 14.5 | 14.5 | 14.6 | 14.6 | 14.7 | 14.7 | 14.7 | 14.6 | 14.6 | 14.3 | 13.7 | 14.0 | 11.9 |
| Releasability (g) | 0.8 | 0.5 | 0.45 | 0.43 | 0.43 | 0.42 | 0.43 | 0.4 | 0.4 | 0.38 | 0.37 | 0.3 | 0.3 | 0.3 | 0.2 |
| Packability (sec) | 7 | 5 | 5 | 4.5 | 4 | 5 | 5 | 6 | 6.5 | 7 | 7 | 7 | 7 | 7 | 10 |

1-2: Analysis of Supportability, Packability and Releasability Depending on Hardness of NBR Foam In this test, the supportability, packability and releasability of NBR foam is determined as a function of hardness of NBR foam.

TABLE 3

Supportability, Releasability and Packability of NBR Foam Depending on Hardness

| | Foam hardness before supporting (Asker F) | | | | | | | | | | | |
|---|---|---|---|---|---|---|---|---|---|---|---|---|
| | 5 | 10 | 20 | 30 | 40 | 50 | 60 | 70 | 80 | 90 | 95 | 100 |
| Supportability (g) | 13.9 | 14.0 | 14.5 | 14.5 | 14.7 | 14.7 | 14.7 | 14.7 | 14.7 | 14.2 | 13.8 | 12.0 |
| Releasability (g) | 0.7 | 0.63 | 0.5 | 0.4 | 0.43 | 0.45 | 0.48 | 0.46 | 0.46 | 0.3 | 0.28 | 0.2 |
| Packability (sec) | 10.5 | 9.5 | 7 | 5 | 3 | 3 | 3 | 4 | 4 | 7 | 9 | 13 |

As shown in Table 3, the NBR foam having an Asker F hardness of 20-80 before supporting the contents provides significantly higher packability as compared to the NBR foam having an Asker F hardness of 5 or 100, and shows adequate releasability. Since it is preferred to release an adequate amount (neither too little nor too much) of contents, a release amount of about 0.3-0.5 g per pay-off is regarded as an adequate amount. When the releasability is less than 0.3 g, the amount of contents taken by an applicator is too small to provide a sufficient beauty make-up effect. When the releasability is larger than 0.5 g, agglomeration may occur and an effect of uniform application may be degraded. Although the supportability shows little change depending on hardness, the NBR foam having an Asker F hardness of 20-95 shows higher supportability.

1-3: Analysis of Supportability, Packability and Releasability Depending on Pore Size of NBR Foam The cosmetic composition as shown in Table 1 and the NBR foam having an average pore size of 200-900 μm are used to determine the supportability, releasability and packability as a function of average pore size in the same manner as described in the above item 1-1. The results are shown in Table 4.

TABLE 4

Supportability, Packability and Releasability Depending on Average Pore Size of NBR Foam

| | Average pore size of foam (μm) | | | | | | | | |
|---|---|---|---|---|---|---|---|---|---|
| | 200 | 300 | 400 | 500 | 600 | 700 | 800 | 900 | 1000 |
| Supportability (g) | 14.5 | 14.7 | 14.7 | 14.7 | 14.7 | 14.5 | 14.0 | 13.7 | 12.3 |
| Releasability (g) | 0.22 | 0.32 | 0.37 | 0.4 | 0.43 | 0.45 | 0.47 | 0.55 | 0.75 |
| Packability (sec) | 10 | 5 | 5 | 5 | 4 | 4 | 4 | 3 | 3 |

As shown in Table 4, use of the NBR foam having an average pore size of 200-900 μm provides adequate releasability and high packability. In addition, the NBR foam having an average pore size of 200-600 μm provides the highest supportability.

1-4: Analysis of Supportability and Releasability Depending on Viscosity of Cosmetic Composition NBR foam having an average pore size of 680 μm and an Asker F hardness of 50 before supporting a cosmetic composition is provided. Then, the NBR foam is used to support each of the cosmetic compositions having a viscosity of 1,500-63,000 cps as shown in Table 5 therein, and the supportability and releasability are determined in the same manner as 1-1. As shown in Table 6, a cosmetic composition having a viscosity of 2,000-60,000 cps shows excellent supportability and adequate releasability.

TABLE 5

Constitution of Cosmetic Composition Having Different Density

| Ingredients (Amount, wt %) | | | | | | | | |
|---|---|---|---|---|---|---|---|---|
| Ozokerite | 18 | 15 | 12 | 10 | 6 | 4 | 1 | 1 |
| Dicaprylyl carbonate | 10 | 10 | 10 | 10 | 10 | 10 | 10 | 10 |
| Octylmethoxy cinnamate | 7 | 7 | 7 | 7 | 7 | 7 | 7 | 7 |
| Disteadimonium hectorite | 2.5 | 2.3 | 2 | 2 | 1.7 | 1 | 0.7 | 0.3 |
| Decamethyl cyclopentasiloxane | 16 | 16 | 16 | 16 | 16 | 16 | 16 | 16 |
| Sorbitan sesquioleate | 2 | 2 | 2 | 2 | 2 | 2 | 2 | 2 |
| Lauryl PEG. PPG-18.18methicon | 1.5 | 1.5 | 1.5 | 1.5 | 1.5 | 1.5 | 1.5 | 1.5 |
| Polymethyl methacrylate | 5 | 5 | 5 | 5 | 5 | 5 | 5 | 5 |
| Titanium dioxide/iron oxide | 7 | 7 | 7 | 7 | 7 | 7 | 7 | 7 |
| Water | To 100 | To 100 | To 100 | To 100 | To 100 | To 100 | To 100 | To 100 |
| Glycerin | 8 | 8 | 8 | 8 | 8 | 8 | 8 | 8 |
| Salt | 1 | 1 | 1 | 1 | 1 | 1 | 1 | 1 |
| Viscosity | 63,000 cps | 60,000 cps | 51,000 cps | 50,000 cps | 30,000 cps | 10,000 cps | 2,000 cps | 1,500 cps |

TABLE 6

Packability, Supportability and Releasability Depending on Viscosity of Cosmetic Composition

| | Viscosity (cps) | | | | | | |
|---|---|---|---|---|---|---|---|
| | 1500 | 2000 | 10000 | 30000 | 50000 | 60000 | 63000 |
| Supportability (g) | 14 | 14.8 | 14.7 | 14.5 | 13.7 | 13.0 | 12.5 |
| Releasability (g) | 0.26 | 0.40 | 0.42 | 0.42 | 0.44 | 0.44 | 0.45 |

1-5: Antibacterial Effect of NBR Foam

The antibacterial effect is determined by measuring a ratio of decrease in *staphylococcus* and *pneumonia* after inoculation. In this antibacterial test, the test method of KSK0693 is used and the test strain includes *Staphylococcus aureus* ATCC 6538, *Klebsiella pneumonia* ATCC 4352. The results are shown in Table 7.

TABLE 7

Antibacterial effect of NBR foam

|  | NBR Foam |
|---|---|
| Cytostatic decrease of *Staphylococcus* | 99% |
| Cytostatic decrease of Pneumonia | 99% |

1-6: Comparison of Supportability, Color Developability, Moisturizing Effect and Covering Effect Between NBR Foam and Polyurethane NBR foam having an average pore size of 600 μm, an Asker F hardness of 50 and a size of circle diameter 44 mm×height 9.0 mm is provided. As control, polyurethane (95 ppi) having a size of circle diameter 44 mm×height 9.0 mm is used as a carrier in which a cosmetic composition is supported.

As shown in Table 8, when a cosmetic composition having a low viscosity (2000 cps) is supported, the NBR foam carrier shows higher supportability as compared to the polyurethane carrier.

When a cosmetic composition having high viscosity is supported, as shown in Table 9, the NBR foam carrier shows higher packability (5 seconds) as compared to the polyurethane carrier (20 seconds), and provides higher moisturizing and covering effects.

TABLE 8

Comparison of Supportability and Color Developability of Low-Viscosity Cosmetic Composition Depending on Carrier Type

|  | Polyurethane 95 ppi | NBR | Reference |
|---|---|---|---|
| Supportability of low-viscosity (2000 cps) cosmetic composition (g) | 13.5 | 14.5 | NBR shows higher supportability |
| Color developability of low-viscosity (2000 cps) cosmetic composition * | 5 | 9 | NBR shows higher color developability |

* Color developability: 1, 3, 5, 6, 9, a higher number means higher color developability

TABLE 9

Comparison of Packability, Moisturizing Effect and Covering Effect of High-Viscosity Cosmetic Composition Depending on Carrier Type

|  | Polyurethane 95 ppi | NBR |
|---|---|---|
| Packability of high-viscosity (50,000 cps) cosmetic composition (sec) | 20 | 5 |
| Moisturizing effect of high-viscosity (50,000 cps) cosmetic composition ** | 7 | 9 |
| Covering effect of high-viscosity (50,000 cps) cosmetic composition *** | 5 | 9 |

** Moisturizing effect: 1, 3, 5, 7, 9, a higher number means higher moisturizing effect
*** Covering effect: 1, 3, 5, 7, 9, a higher number means higher covering effect.

[Test Example 2] Comparison of NBR Foam Depending on Pore Size 2-1: Determination of Packability to Cosmetic Composition One NBR foam having an average pore size of 150 μm, an Asker F hardness of 50 before supporting a cosmetic composition and a size of circle diameter 44 mm×height 9.0 mm and another NBR foam having an average pore size of 600 μm, an Asker F hardness of 50 before supporting a cosmetic composition and a size of circle diameter 44 mm×height 9.0 mm are used to pack the cosmetic compositions as shown in Tables 10 and 11.

TABLE 10

| Item | | Ingredients (Amount wt %) | Sample 1 | Sample 2 | Sample 3 | Sample 4 |
|---|---|---|---|---|---|---|
| Oil phase Ingredients | Oily ingredients | Ozokerite | 10.0 | 10.0 | 5.0 | 1.0 |
| | | Dicaprylyl carbonate | 10.00 | 10.00 | 10.00 | 10.00 |
| | UV protecting agent | Octylmethoxy cinnamate | 7.000 | 7.000 | 7.000 | 7.000 |
| | Thickening agent | Disteadimonium hectorite | 3.00 | 2.00 | 1.50 | 1.50 |
| | Oily ingredients | Decamethylcyclopentasiloxane | 16.00 | 16.00 | 16.00 | 16.00 |
| | Emulsifier | Sorbitan sesquioleate | 2.000 | 2.000 | 2.000 | 2.000 |
| | | Lauryl PEG. PPG-18. 18methicon | 1.500 | 1.500 | 1.500 | 1.500 |
| | Pigment | Polymethyl methacrylate | 5.00 | 5.00 | 5.00 | 5.00 |
| | | Titanium dioxide/iron oxide | 7.00 | 7.00 | 7.00 | 7.00 |
| Aqueous phase Ingredients | | Water | To 100 | To 100 | To 100 | To 100 |
| | Moisturizing agent | Glycerin | 8.000 | 8.000 | 8.000 | 8.000 |

TABLE 10-continued

| Item | Ingredients (Amount wt %) | Sample 1 | Sample 2 | Sample 3 | Sample 4 |
|---|---|---|---|---|---|
| Emulsion stabilizer | Salt | 1.00 | 1.00 | 1.00 | 1.00 |
|  | Fragrance | 0.200 | 0.200 | 0.200 | 0.200 |
|  | Total | 100.000 | 100.000 | 100.00 | 100.00 |

TABLE 11

Composition of Eyeliner Ingredients

| Ingredients | Sample 5 (Amount wt %) |
|---|---|
| Purified water | Balance |
| Hydroxyethyl cellulose | 1.0 |
| Triethanolamine | 4.0 |
| Black iron oxide | 1.0 |
| Carbon black | 3.0 |
| Ceteth-25 | 0.5 |
| Steareth-20 | 0.5 |
| Bees wax | 6.0 |
| Carnauba wax | 4.0 |
| Paraffin | 4.0 |
| Stearic acid | 7.5 |
| Glyceryl monostearate | 1.0 |
| Polysorbate | 2.0 |
| Acrylate copolymer emulsion | 23.0 |

The samples of Table 10 and Table 11 have the viscosity as shown in Table 12.

TABLE 12

|  | Sample 1 | Sample 2 | Sample 3 | Sample 4 | Sample 5 |
|---|---|---|---|---|---|
| Viscosity(cps) | Cake formulation | 45,000 cps | 23,000 cps | 4,000 cps | 4,000 cps |
| Measurement method | SUN RHEOMETER CR-500DX Adaptor 25 | BROOKFIELD RVDV-III ULTRA (Serial No. RY6521152) 63spindle 5 rpm 30° C. 60 sec | BROOKFIELD RVDV-III ULTRA (Serial No. RY6521152) 63spindle 5 rpm 30° C. 60 sec | BROOKFIELD RVDV-III ULTRA (Serial No. RY6521152) 63spindle 5 rpm 30° C. 60 sec | BROOKFIELD RVDV-III ULTRA (Serial No. RY6521152) 63spindle 5 rpm 30° C. 60 sec |

Each of the cosmetic compositions of Samples 1-5 is supported in the NBR foam (Comp. Ex.) having an average pore size of 150 µm and the NBR foam (Ex.) having an average pore size of 600 µm, and the packability to an adequate amount of contents within a predetermined time is determined. The results are shown in Table 13.

TABLE 13

| Packability (sec) | Sample 1 | Sample 2 | Sample 3 | Sample 4 | Sample 5 |
|---|---|---|---|---|---|
| Viscosity | Cake formulation | 45,000 cps | 23,000 cps | 4,000 cps | 4,000 cps |
| Comp. Ex. | >30 sec | >30 sec | 20 sec | 3 | 3 |
| Ex. | 7 | 5 | 4 | 3 | 3 |

2-2. Determination of Long-Term Supportability to Cosmetic Composition

First, 15 g of each of the cosmetic compositions of Samples 1-5 is packed in each of the NBR foam (Comp. Ex.) having an average pore size of 150 µm and the NBR foam (Ex.) having an average pore size of 600 µm, and allowed to stand at 55° C. for 4 weeks. Then, the amount of cosmetic composition carried by the carrier in a container is measured. As shown in Table 14, the NBR foam according to each of Example and Comparative Example has high supportability.

TABLE 14

| Supportability (g) | Sample 1 | Sample 2 | Sample 3 | Sample 4 | Sample 5 |
|---|---|---|---|---|---|
| Viscosity | Cake formulation | 45,000 cps | 23,000 cps | 4,000 cps | 4,000 cps |
| Comp. Ex. | 14.2 | 14.3 | 14.3 | 14.0 | 14.0 |
| Ex. | 14.6 | 14.7 | 14.6 | 14.5 | 14.5 |

2-3: Determination of Releasability to Cosmetic Composition

Each of the NBR foam having an average pore size of 150 μm and the NBR foam having an average pore size of 600 μm is evaluated in a releasability test. When the cosmetic composition supported in each carrier is taken by an applicator, the amount of cosmetic composition taken per pay-off is measured. As shown in FIG. 4, the NBR foam having an average pore size of 600 μm has excellent releasability.

2-4: Determination of Color Developability and Covering Effect of Cosmetic Composition After supporting the same foundation (Sample 2) and eyeliner (Sample 5) in each of the NBR foam having an average pore size of 150 μm and the NBR foam having an average pore size of 600 μm, the color developability is compared between the two types of foam.

The NBR foam having an average pore size of 150 μm allows foundation to develop a thin and cloudy color, while the NBR foam having an average pore size of 600 μm shows excellent color developability, covering and moisturizing effects, application feel and elasticizing effect.

In the case of eyeliner, the NBR foam having an average pore size of 150 μm shows a thin and cloudy eye line, while the NBR foam having an average pore size of 600 μm shows a dark and clear eye line.

TABLE 15

| | NBR foam having an average pore size of 150 μm | NBR foam having an average pore size of 600 μm |
|---|---|---|
| Foundation | Cloudy and natural color development | Color development with covering effect |
| Eye liner | Thin and cloudy eye line | High-color developability and high-concentration eye line |

[Test Example 3] Evaluation of Quality of NBR Foam

First, NBR as a main ingredient, a pigment, a vulcanizing agent, and optionally a foaming agent and other additives are compounded with water at a predetermined ratio and blended under agitation to carry out foaming. Next, the foamed product is introduced to and cured in a mold, heated in a heating furnace to carry out vulcanization simultaneously with molding. Then, the resultant product is cut, dried and surface treated to provide NBR foam.

The thus obtained NBR foam has an Asker hardness of 47 and an average pore size of 680 μm.

Then, the supportability, packability and releasability of the NBR foam are determined.

A cosmetic composition having a viscosity of 12,800 cps is provided to have the same composition as shown in Table 1, and then is supported in the NBR foam. As a result, the NBR foam shows a diameter swelling ratio of 12.90% and a height swelling ratio of 13.20%.

The packability is determined as the time required for packing 15 g of the cosmetic composition. Initial packing is not perfect due to the characteristics of NBR, but NBR spontaneously swells and is wet after packing the cosmetic composition. Thus, the cosmetic composition is introduced to a container along with a carrier and allowed to be packed in the carrier without overflow.

The supportability is determined by measuring the amount of cosmetic composition carried by the carrier in a container after packing 15 g of the cosmetic composition in NBR foam and allowing the NBR foam to stand at 55° C. for 4 weeks. The releasability is determined by measuring the amount of contents when taking the contents by a hand or puff from each type of foam.

The results are shown in Table 16.

TABLE 16

| Viscosity of Cosmetic composition | 12,800 cps |
|---|---|
| Hardness of carrier | 47 |
| Average pore size of carrier | 680 μm |
| Packability (sec) | 9 |
| Supportability (g) | 13.5 |
| Releasability (g) | 0.22 |
| Diameter swelling ratio | 12.90% |
| Height swelling ratio | 13.20% |

[Preparation Example 1] Eyeliner

In this example, the eyeliner has a viscosity of 2,000-30,000 cps as determined under the conditions of spindle No. 63 and spindle speed of 5 rpm.

TABLE 17

| Ingredients | Preparation Ex. 1 (Amount wt %) |
|---|---|
| Purified water | Balance |
| Hydroxyethyl cellulose | 1.0 |
| Triethanolamine | 4.0 |
| Black iron oxide | 1.0 |
| Carbon black | 3.0 |
| Ceteth-25 | 0.5 |
| Steareth-20 | 0.5 |
| Bees wax | 6.0 |
| Carnauba wax | 4.0 |
| Paraffin | 4.0 |
| Stearic acid | 7.5 |
| Glyceryl monostearate | 1.0 |
| Polysorbate | 2.0 |
| Acrylate copolymer emulsion | 23.0 |

[Preparation Example 2] Lip Make-Up

In this example, the lip make-up has a viscosity of 5,000-60,000 cps as determined under the conditions of spindle No. 63 and spindle speed of 5 rpm.

TABLE 18

| Ingredients | Preparation Ex. 2 (Amount wt %) |
|---|---|
| Sorbitan stearate | 3.0 |
| Sodium acrylate copolymer | 0.3 |
| Dimethicone/vinyldimethicone crosspolymer | 5.0 |
| Purified water | 10.0 |
| Glycerin | 5.0 |
| Sodium hyaluronate | 2.0 |
| Candelilla wax | 2.0 |
| Polyethylene | 4.0 |
| Bees wax | 7.0 |
| Caprylic/capric glyceride | 10.0 |
| Diisostearyl maleate | to 100 |
| Polyglyceryl-2 triisostearate | 8.0 |
| Diphenyldimethicone | 5.0 |
| Phytosteryl/isostearyl/cetyl/stearyl/behenyl dimer dilinoleate | 8.0 |
| Colorant, extender pigment, pearl | Qsad |

[Preparation Example 3] Skin Care

In this example, the skin care composition has a viscosity of 3,000-50,000 cps as determined under the conditions of spindle No. 63 and spindle speed of 5 rpm.

TABLE 19

| Ingredients | Preparation Ex. 3 (Amount, wt %) |
|---|---|
| Purified water | to 100 |
| Glycerin | 8.0 |
| Butylene glycol | 4.0 |
| Liquid paraffin | 15.0 |
| Betaglucan | 7.0 |
| Carbomer | 0.1 |
| Hexamidine and retinoid | 1.0 |
| Caprylic/capric triglyceride | 3.0 |
| Squalane | 1.0 |
| Cetearyl glucoside | 1.5 |
| Sorbitan stearate | 0.4 |
| Cetearyl alcohol | 1.0 |
| Preservative | Qsad |
| Fragrance | Qsad |
| Colorant | Qsad |
| Bees wax | 3.0 |

While the exemplary embodiments have been shown and described, it will be understood by those skilled in the art that various changes in form and details may be made thereto without departing from the scope of this disclosure as defined by the appended claims. Therefore, it is intended that the scope of the present disclosure includes all embodiments falling within the spirit and scope of the appended claims.

What is claimed is:

1. A cosmetic product, comprising:
   a foam carrier; and
   a cosmetic composition supported in the foam carrier,
   wherein the foam carrier comprises acrylonitrile-butadiene rubber (NBR), and
   wherein the foam carrier comprises pores and said pores have bumps at a framework of a large-size cell of a cell-in-cell structure.

2. The cosmetic product according to claim 1, wherein the foam carrier is provided with pores having an average size of 200-900 μm.

3. The cosmetic product according to claim 1, wherein foam carrier has an Asker F hardness of 10-95 before supporting the cosmetic composition.

4. The cosmetic product according to claim 1, wherein the pores having bumps are present at a ratio of 20-80% based on the total number of pores contained in the foam carrier.

5. The cosmetic product according to claim 1, wherein the bumps have a size corresponding to 2.5-25% based on the average pore size.

6. The cosmetic product according to claim 1, wherein the foam carrier has at least one of the following characteristics:
   i) a height swelling ratio of 2-25% after supporting the cosmetic composition; and
   ii) a diameter swelling ratio of 2-25% after supporting the cosmetic composition, and
   the height swelling ratio and diameter swelling ratio are calculated according to the following Mathematical Formulae 1 and 2:

Height swelling ratio (%)=(Height of carrier after supporting contents−Initial height of carrier)/ Initial height of carrier*100      [Mathematical Formula 1]

Diameter swelling ratio (%)=(Diameter of carrier after supporting contents−Initial diameter of carrier)/Initial diameter of carrier*100,      [Mathematical Formula 2]

7. The cosmetic product according to claim 1, wherein the foam carrier has an Asker F hardness of 10-100 before supporting the cosmetic composition.

8. The cosmetic product according to claim 1, wherein the foam carrier has at least one of the following characteristics:
   i) a packability of 3-10 seconds, wherein the packability is defined as the time required for packing 15 g of cosmetic composition manually in the foam carrier;
   ii) a supportability of 85-99% based on the total weight of cosmetic composition packed in the foam carrier, wherein the supportability is defined as the amount of cosmetic composition carried by the foam carrier after packing the cosmetic composition therein; and
   iii) a releasability of 0.2-0.7 g, wherein the releasability is defined as the amount of cosmetic composition taken from the foam carrier per pay-off.

9. The cosmetic product according to claim 1, wherein the cosmetic composition supported in the foam carrier is selected from the group consisting of solution, emulsion, gel, cream and suspension.

10. The cosmetic product according to claim 1, wherein the cosmetic composition supported in the foam carrier is selected from the group consisting of skincare cosmetics, pigment-containing make-up cosmetics, haircare cosmetics and UV protecting agents.

11. The cosmetic product according to claim 1, wherein the foam carrier has a coating film on at least one surface other than the surface that is in contact with a hand or applicator.

12. The cosmetic product according to claim 11, wherein the at least one surface is a lateral surface or bottom surface.

13. The cosmetic product according to claim 1, which further comprises an applicator by which the cosmetic composition is taken from the carrier having the cosmetic composition supported therein.

14. The cosmetic product according to claim 1, wherein the cosmetic composition has a viscosity of 2,000-60,000 cps.

15. The cosmetic product according to claim 1, wherein the foam carrier has a thickness of 1-50 mm.

16. The cosmetic product according to claim 1, wherein the foam carrier has a releasability of 0.2-0.7 g, wherein the releasability is defined as the amount of said cosmetic composition taken from the foam carrier per pay-off when compressing the surface of NBR foam carrier including the cosmetic composition having a viscosity of 2,000-60,000 cps supported therein and having a size of circle diameter 44 mm×height 9.0 mm under a force of 2 kg.

\* \* \* \* \*